United States Patent [19]

Brown

[11] 4,234,576
[45] Nov. 18, 1980

[54] PHENOXYBENZYLPHOSPHONIUM SALT PESTICIDES

[75] Inventor: Michael J. Brown, Randolph Township, Morris County, N.J.

[73] Assignee: GAF Corporation, New York, N.Y.

[21] Appl. No.: 27,609

[22] Filed: Apr. 5, 1979

Related U.S. Application Data

[63] Continuation-in-part of Ser. No. 861,204, Dec. 16, 1977, Pat. No. 4,162,313.

[51] Int. Cl.$^2$ .............................................. A01N 9/36
[52] U.S. Cl. ................................... 424/211; 424/214; 424/217
[58] Field of Search ............................... 424/211, 214

[56] References Cited

U.S. PATENT DOCUMENTS

| | | | |
|---|---|---|---|
| 3,642,989 | 2/1972 | Martin et al. | 424/211 |
| 3,804,950 | 4/1974 | Diamond | 424/198 |

Primary Examiner—Allen J. Robinson
Attorney, Agent, or Firm—M. J. Maue; W. C. Kehm

[57] ABSTRACT

The pesticidal compounds having the formula:

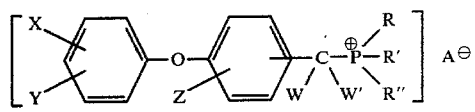

wherein $A^\ominus$ is a halogen anion; X, Y and Z are each independently hydrogen, a halogen atom or haloalkyl group of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen; W is —CHO or —CHN(R''')$_2$ where each R''' is independently hydrogen or alkyl of from 1 to 4 carbon atoms, optionally substituted with halogen; and W' is hydrogen or may represent a bond forming a double bond between C and W. The invention also relates to the method of preparing formulations or compositions of said pesticides together with a method for their application.

15 Claims, No Drawings

PHENOXYBENZYLPHOSPHONIUM SALT PESTICIDES

This application is a continuation-in-part of application Ser. No. 861,204 filed Dec. 16, 1977, now U.S. Pat. No. 4,162,313, the disclosure of which is incorporated herein.

This application relates to a new class of pesticidal compounds, a process for their preparation and the application of said compounds utilized either alone as an agricultural chemical or in chemical formulations with a carrier and optionally other agricultural chemicals which do not materially lower the activity of the present pesticides.

The compounds of this invention find utility as pesticides having particular efficacy as insecticides which are ecologically safe and leave no toxic residue in the plants and are not toxic to humans.

For the purpose of the present disclosure, the term pesticide is intended to include insecticides.

It is an object of this invention to provide new and useful pesticides which are not harmful to the environment.

Still another object is to provide novel insecticides for coleopterous insects and other pests.

Another object is to provide novel nematocides.

Another object of the present invention is to provide insecticides having a high selectivity for beetles, while having substantially no detrimental effect on crops.

Yet another object of this invention is to provide formulations for the present pesticides for applications as sprays or dusts.

These and other objects of the present invention will become apparent from the following description and disclosure.

According to this invention, there is provided phosphonium salt pesticide having the formula:

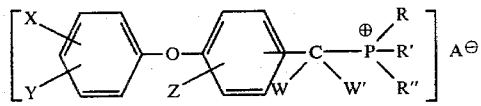

wherein $A^{\ominus}$ is a halogen anion; X, Y and Z are each independently hydrogen, a halogen atom or a haloalkyl group of from 1 to 4 carbon atoms; R, R' and R" are each independently phenyl, halophenyl, haloalkylphenyl of from 7 to 12 carbon atoms or alkyl of from 1 to 6 carbon atoms, optionally substituted with halogen; W is —CHO or —CHN(R''')₂ where each R''' is independently hydrogen or alkyl of from 1 to 4 carbon atoms, optionally substituted with halogen; and W' is hydrogen or may represent a bond forming a double bond between C and W. The halogen referred to in the above phosphonium salt compounds is fluorine, chlorine, bromine or iodine.

Of the above group of compounds, those wherein one of X or Y is hydrogen and the other is a halogen or perhaloalkyl, R, R' and R" are the same and are either lower alkyl or phenyl and $A^{\ominus}$ is a bromine or chlorine anion are preferred as pesticides in the present invention.

The preparation of the present amino and formaldehyde derivatives of phenoxy benzyl phosphonium salts is described in copending parent application Ser. No. 861,204, filed Dec. 16, 1977 now U.S. Pat. No. 4,162,313. Generally, the amino derivative is obtained by reacting the phenoxybenzyl phosphonium halide with an amino-dimethoxymethane in an anhydrous alcoholic solution, e.g. an anhydrous solution of ethanol, propanol, butanol, pentanol, or another inert organic solvent. This reaction is carried out at a temperature of between about 10° C. and about 180° C. under from about 5 psi to about 30 psi, preferably at a temperature between about 80° C. and about 140° C. under atmospheric pressure. The following Equation I exemplifies such a viable process for the preparation of the amino substituted phosphonium compounds of the present invention.

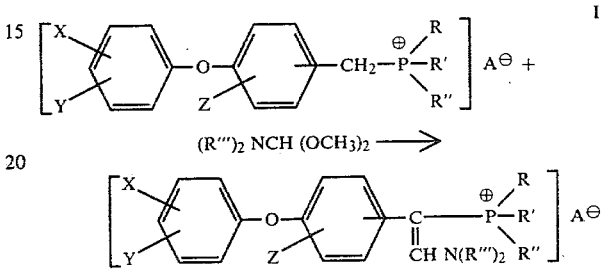

In the above equations, X, Y, Z, R, R', R" and R''' have the meaning set forth in Formula I of the preceding disclosure.

The above amino substituted product is recovered from the reaction mixture by evaporation to dryness to remove alcoholic by-product and trituration with petroleum ether, cyclohexane or any other inert agent conventionally employed for forming a fine particulate solid or powder.

To obtain the aldehyde derivative of the phosphonium salt of the present invention, the product of Equation I is reacted with an aqueous solution of mineral acid such as a 2 to 50% solution of HCl, H₂SO₄, HNO₃, etc., at a temperature of between about 25° C. and about 100° C. under from about 5 psig to about 30 psig; preferably between about 50° C. and about 80° C. under atmospheric pressure. The corresponding aldehyde substituted phosphonium compound is formed within a period of from about 15 minutes to about 1.5 hours and is recovered from the reaction mixture by extraction with chloroform or another inert organic solvent conventionally employed for removing acid impurities. The solvent is then evaporated and the product triturated with a suitable agent, such as petroleum ether.

The following Equation II illustrates such a viable process for the preparation of the aldehyde derivative of the phenoxybenzyl phosphonium halide.

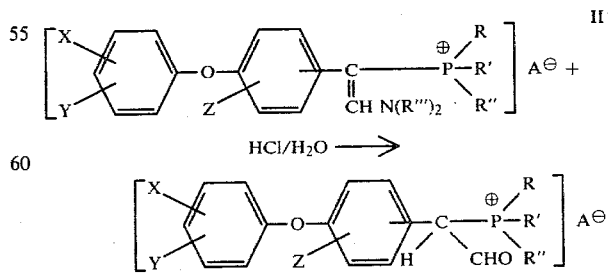

The product of Equation II may be converted into the corresponding dehydrohalogenated compound as shown in Equation III. The conversion is effected by passing the aldehyde substituted phosphonium compound (e.g. the product of Equation II) downwardly through an anion exchange column (e.g. Amberlite CG-4B, 200–400 mesh) in an alcohol solution, e.g. a methanol solution, at ambient temperature. The product is then isolated by evaporation to dryness followed by trituration with cyclohexane or petroleum ether or any other conventional trituration liquid. As indicated, the product of Equation III exists in equilibrium.

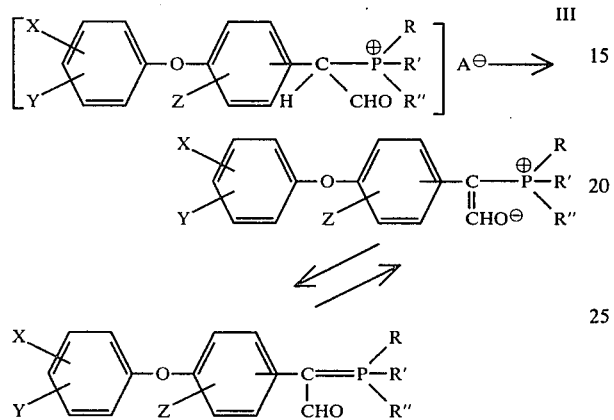

The following compounds shown in Table I are representative of the novel compounds of the present invention.

TABLE I

| Compound Number | Structure | °C. Melt Pt. |
|---|---|---|
| 1 | [Cl-C6H3-O-C6H4-C(=CHN(C2H5)2)-P(C4H9)3]⊕ Cl⁻ | 120–125 |
| 2 | [Cl-C6H3-O-C6H4-C(C=CHN(CH3)2)(P(C6H5)3)]⊕ Br⁻ | 50–8 |
| 3 | [Cl-C6H3-O-C6H4-C(CH—CHO)(P(C6H5)3)]⊕ Br⁻ | 184–8 |
| 4 | [Cl-C6H3-O-C6H4-C(C=CHO⁻)(P(C6H5)3)]⊕ | 75 |
| 5 | [C6H5-O-C6H3(Cl)-C(C—CHO)(P(C6H5)3)]⊕ Br⁻ | 92–103 |

A. PREPARATION OF COMPOUND 1 IN TABLE I

Chlorophenoxybenzyl tributyl phosphonium chloride having the formula

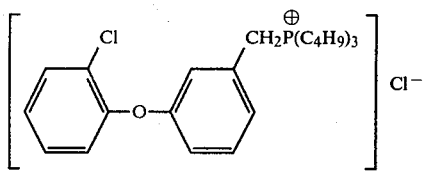

(8 g) was dissolved in 35 ml of anhydrous propanol and introduced into a reactor. This solution was heated to 110° C. and 9 g of diethylaminodimethoxymethane was added. The reaction mixture was maintained at 110° C. and agitated for 35 hours at atmospheric pressure. The resulting reaction mixture was then evaporated to remove the solvent and triturated with 110 ml petroleum ether, after which it was dried to provide 10 g of product.

B. PREPARATION OF COMPOUND 2 IN TABLE I

Chlorophenoxybenzyl triphenylphosphonium bromide having the formula

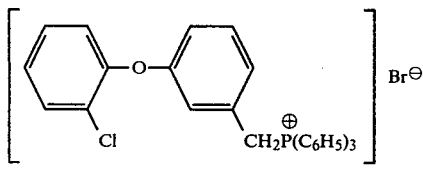

(5 g) was dissolved in 30 ml of anhydrous propanol and introduced into a reactor. This solution was heated to 110° C. and 5.5 g of dimethylaminodimethoxymethane was added. The reaction mixture was maintained at 110° C. and agitated for 32 hours at atmospheric pressure. The resulting reaction mixture was then evaporated to remove the solvent and triturated with 100 ml petroleum ether, after which it was dried to provide 3.5 g of product.

It is to be understood that any of the corresponding fluoride, chloride or iodide phosphonium salts or any such salts of compounds 1 or 2 can be substituted in the above preparations to provide the corresponding halogen-containing phenoxy benzyl phosphonium halide salt.

C. PREPARATION OF COMPOUND 3 OF TABLE I

Chlorophenoxystyryl -N,N-dimethylamino-triphenyl phosphonium bromide having the formula

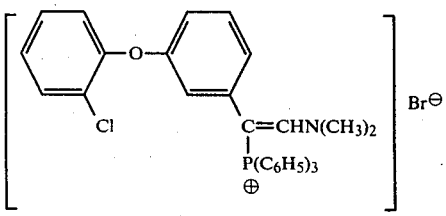

(22 g) was introduced into a reactor wherein it was contacted with 165 ml of a 2 normal aqueous solution of hydrochloric acid at a temperature of 60° C. under atmospheric pressure for a period of 0.75 hour. The resulting product was then recovered by extraction with 200 ml of chloroform at room temperature and the chloroform vaporized by vacuum evaporation. The product is then triturated with petroleum ether to yield 10 g of product of over 95% purity.

It is to be understood that any of the corresponding fluoride, chloride or iodide phosphonium salts of the halogen-containing phenoxy styryl amino phosphonium bromides described in preparation B can be substituted in the above Preparation C to provide the corresponding aldehyde of the phosphonium salt.

D. PREPARATION OF COMPOUND 5 OF TABLE I

The procedure in preparation C is repeated except that phenoxy(chlorostyryl)-N,N-dimethylamino triphenyl phosphonium bromide having the formula

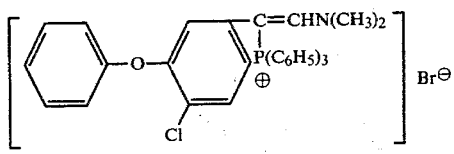

is substituted for the phosphonium compound in C, and 9.5 g of product recovered.

E. PREPARATION OF COMPOUND 4 OF TABLE I

Chlorophenoxybenzylaldehyde-triphenylphosphonium chloride having the formula

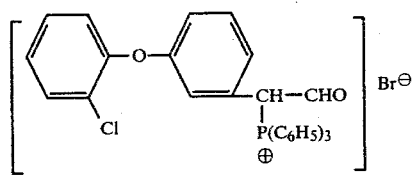

(5 g) was dissolved in methanol (25 ml) and passed through a column of amberlite anion exchange resin (8.5 g of CG-4B, 200-400 mesh). After eluting the column with a further 20 ml of methanol the combined effluent was evaporated to dryness and the resulting oil triturated with cyclohexane (50 ml) and petroleum ether (50 ml) to yield 3 g of product.

It is understood that any of the corresponding fluoride, chloride or iodide phosphonium salts of the halogen-containing aldehyde described in preparation B can be substituted in the above preparation E to provide the corresponding dehydrohalogenated compound.

The compounds of the present invention can be applied alone as pesticides or can be employed in combination with an adjuvant in either liquid or solid form. The compositions containing the compounds of the present invention are prepared by admixing one or more of the present pesticides or one of the present pesticides with one or more of those disclosed in copending application Ser. No. 861,204 with the adjuvant including diluents, extenders, carriers or conditioning agents to provide compositions in the form of finely divided particulate solids, granules, pellets, wetable powders, dusts, solutions and aqueous dispersions or emulsions. Illustrative of the granular solid carriers and extenders which may be employed include the talcs, clays, diatomaceous earth, silica, pumice, sulphur, walnut or coconut flour, wood dust, tobacco dust, charcoal and the like. Illustrative of the liquid carriers and extenders are water, propyleneglycol, N-methyl-pyrrolidone, benzene, xylene, cyclohexane and other liquid paraffins, acetone, methylethylketone, ethylketone, and other known extenders and carriers which may be employed singly or in combination. The formulations may also include a minor amount up to 8% of a surfactant which includes wetting agents, dispersing agents, suspending agents, and emulsifying agents. Typical of this group are the polyoxyethylene derivatives of fatty acid esters, imidazolines, etc. It is also to be understood that the formulations of the present invention may include other biocidally active components to achieve additional biocidal effects. Such combinations include mixtures of the present compounds with, e.g. Ethephon, Phosphon, Nitrofen, triacontanol, or other biocidally active compounds.

In selecting the appropriate rate of application of the present pesticides, it should be understood that the precise rates will be somewhat dependent upon the mode of application, such as soil incorporation, and pre-emergent or post-emergent plant treatment and foilar dusting or drench. Generally, for beneficial effects, the present compound or a mixture of the present compounds is applied in amounts of from about 0.05 to about 25 pounds per acre, or more. Preferably, applications of from about 0.1 to about 10 pounds per acre of active ingredient is employed. The concentration of the present compound either employed alone or in a formulation is between about 5 ppm and about 3,000 ppm, per plant, or an effective dosage for at least 50% plant response for the effect desired.

Having thus generally described the invention, reference is now had to the accompanying examples which serve to illustrate preferred and specific embodiments, but which are not to be construed as unduly limiting to the scope of the present invention as defined in the foregoing specification and in the appended claims. In the following examples, all amounts are by weight unless otherwise indicated. It is to be understood, that any of the foregoing compounds of this invention, as defined in Formula I which are not exemplified in the following examples, can be substituted therein to provide the beneficial effects reported therein and good product yield.

EXAMPLES 1 THROUGH 4

The activity of compounds listed in Table I were tested as pesticides against two widely divergent species, namely, the Mexican Bean Beetle and Southern Armyworm.

The pesticidal activity of the test compounds for beetles was examined at a dosage level of 250 ppm concentration of compound in solution. The solutions containing the test compound were prepared by introducing the compound as a solution of 90% water, 10% acetone containing 100 ppm Triton X-155 as a surfactant and then diluting the resulting solution with water to the required concentration, namely, to 250 ppm as reported in Table II.

For each compound tested, leaves of young bean plants from the same seed source and growing in sterilized soil under uniform conditions, were employed. Several leaves of these plants were removed by cutting the petioles, after which the severed leaves were dipped in the solution of test compound, (Group A). The petioles of the excised leaves were placed in a water reservoir to maintain leaf turgidity. After the solutions on the first group of leaves (A) had dried, 5 larvae of the Mexican Bean Beetle were placed on each leaf. Observations on the mortality and the extent of inhibition of feeding of the beetles was made on an average of 2 to 3 days after infestation with the larvae and results reported in Table II. Both of these responses were rated from 0 (no effect on mortality or inhibition of feeding) to 100 (complete destruction of the larvae and consequent total inhibition of feeding). Similarly, after the solutions on the second group of excised plant leaves had dried, the leaves were infested with South Armyworm larvae (Group B) by placing 5 larvae on each of the treated leaves. Again, observations were averaged for 2–3 days after infestation and results reported in Table II. The test compound numbers in the following tables correspond with the numbers assigned to specific compounds in Table I. Because of the high activity of compound 2, the above tests were repeated for compound 2, on Mexican Bean Beetle except that the dosage level was reduced to as little as 33 ppm. The results of this test are reported in Table III.

| | | TABLE II | | | |
|---|---|---|---|---|---|
| | | Dosage Level - 250 ppm Test Compound | | | |
| | | Mexican Bean Beetle (A) | | Southern Armyworm (B) | |
| Example No. | Compound No. | % Kill | % Feeding Inhibition | % Kill | % Feeding Inhibition |
| 1 | 2 | 90 | 60 | 0 | 40 |
| 2 | 3 | 70 | 60 | — | — |
| 3 | 4 | 60 | 60 | — | — |

| | TABLE III | | | |
|---|---|---|---|---|
| | Dosage Level - 33 ppm Test Compound | | | |
| 4 | 2 | 15 | 25 | — | — |

What is claimed is:

1. A process for controlling plant insects which comprises contacting said insects with an insecticidally effective amount of a compound having the formula:

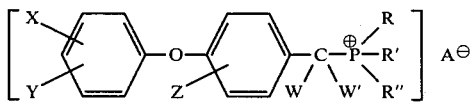

wherein A⊖ is a halogen anion; X, Y and Z are each independently hydrogen, a halogen atom or haloalkyl group of from 1 to 4 carbon atoms; R, R' and R'' are each independently phenyl, halophenyl, haloalkylphenyl of from 7 to 12 carbon atoms or alkyl of from 1 to 6 carbon atoms, optionally substituted with halogen; W is —CHO or —CHN(R''')$_2$ where each R''' is independently hydrogen or alkyl of from 1 to 4 carbon atoms, optionally substituted with halogen; and W' is hydrogen or represents a bond forming a double bond between C and W.

2. The process of claim 1 wherein said compound is at least one in which R, R' and R'' are phenyl radicals; X is hydrogen and Y is a substitutent other than hydrogen.

3. The process of claim 1 wherein said compound is at least one in which R, R' and R'' are the same and are lower alkyl of C$_1$ to C$_6$ carbon atoms.

4. The process of claim 1 wherein said compound is a compound having the formula:

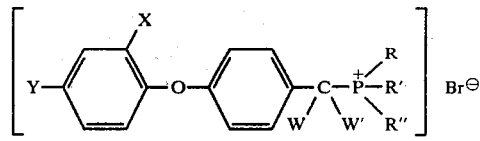

wherein X is hydrogen or chlorine; Y is hydrogen or trifluoromethyl, and wherein one of X and Y is other than hydrogen.

5. The process of claim 1 wherein said compound is a compound having the formula:

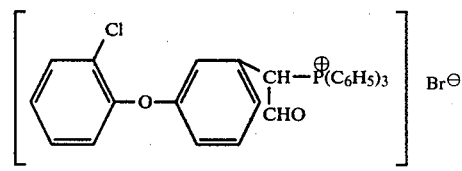

6. The process of claim 1 wherein said compound is a compound having the formula:

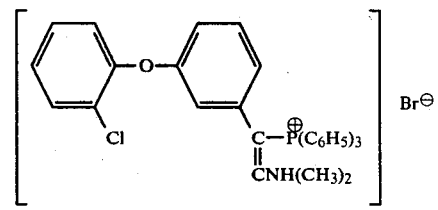

7. The process of claim 1 wherein said compound is a compound having the formula:

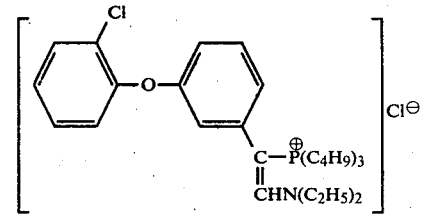

8. The process of claim 1 wherein said compound is a compound having the formula:

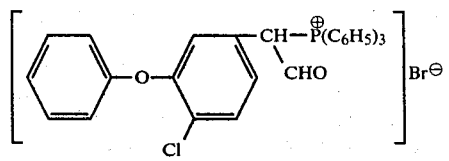

9. The process of claim 1 wherein said compound is a compound having the formula:

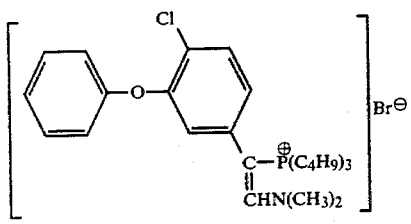

10. The process of claim 1 wherein the compound is mixed with an inert carrier in a concentration of between about 10 ppm and about 10,000 ppm to provide a formulation.

11. The process of claim 10 wherein the formulation is applied at a rate of between about 0.05 and about 25 lbs/acre.

12. The process of claim 1 wherein the compound is mixed with a carrier in a concentration of between about 15 ppm and about 3,000 ppm and is applied at a rate of between about 0.1 and about 10 lbs/acre.

13. The process of claim 12 wherein carrier is a liquid inert carrier and additionally contains a surfactant.

14. The process of claim 10 wherein the carrier is a particulate solid.

15. The process of claim 10 wherein the carrier is an aqueous solution.

* * * * *